United States Patent [19]

Warner et al.

[11] Patent Number: 4,903,695

[45] Date of Patent: Feb. 27, 1990

[54] METHOD AND APPARATUS FOR PERFORMING A KERATOMILEUSIS OR THE LIKE OPERATION

[75] Inventors: John W. Warner, Newtown, Conn.; Francis A. L'Esperance, Jr., Englewood, N.J.

[73] Assignee: LRI L.P., New York, N.Y.

[21] Appl. No.: 278,272

[22] Filed: Nov. 30, 1988

[51] Int. Cl.⁴ ............................................. A61N 5/06
[52] U.S. Cl. ........................................................ 606/4
[58] Field of Search .............. 128/303.1, 362, 345–398

[56] References Cited

U.S. PATENT DOCUMENTS 4,729,372  3/1988  L'Esperance, Jr. .............. 128/303.1

OTHER PUBLICATIONS

"The Potential of an Infrared Hydrogen Fluoride (HF) Laser for Corneal Surgery", by Seiler et al, Lasers in Ophthal. vol. 1 No. 1 (1986) pp. 44–60.
"Advanced Technique in Ophthalmic Microsurgery", by Girard; The C. V. Mosby Company; St. Louis 1981 pp. 159–170.

Primary Examiner—Lee S. Cohen
Assistant Examiner—David Shay
Attorney, Agent, or Firm—Hopgood, Calimafde, Kalil, Blaustein & Judlowe

[57] ABSTRACT

A conventional keratomileusis procedure is modified to the extent that a controlled tissue-ablating laser radiation is applied solely to the freshly cut part of the cornea that is left after severing the lenticle, the radiation being so controlled and characterized as to effect a volumetric removal of exclusively stromal tissue that, upon replacement of the lenticle over the thus-sculptured remainder of the cornea, a new and optically corrected curvature results.

13 Claims, 1 Drawing Sheet

METHOD AND APPARATUS FOR PERFORMING A KERATOMILEUSIS OR THE LIKE OPERATION

BACKGROUND OF THE INVENTION

The invention relates to procedures and apparatus for ophthalmic surgery upon the cornea to correct one or more optical deficiencies of an eye. More particularly, the invention is concerned with controlled use of tissue-ablating laser-beam irradiation of stromal tissue within the optically used central area of the cornea, to effect improved optical performance at the anterior surface of the cornea. And the invention is specifically concerned with the class of surgical procedures which includes keratomileusis and thus a temporary partial or total surgical removal of the lenticle from the cornea.

Origin of keratomileusis and related procedures is attributed to Dr. Jose I. Barraquer, of Bogota, Colombia. His procedures and apparatus are described and illustrated by Dr. Louis J. Girard, in his 1981 authoritative text, "Corneal Surgery", Volume Two, Chapter 6 ("Refractive Keratoplasty"), pp. 143 to 172; Dr. Girard's Chapter 6 concludes with a full bibliography which accounts for the contributions of Dr. Barraquer and others in the art.

It suffices for present purposes to briefly describe Dr. Barraquer's keratomileusis procedure, which is visually employed for surgically correcting a severely myopic eye, although it can also be used to correct for a hyperopia condition. At the outset, a special microtome (a "microkeratome") is applied to the cornea and operates to shear off, as a lenticle, namely, a central front truncation of predetermined size, from the central region of the cornea, the diameter of the truncation being in the order of 7.5 mm and thus fully embracing the optically used region of the cornea. Having selected a holding disc for its concavity adapted to the front-surface curvature of the lenticle, the lenticle is fitted to the concavity, and is then frozen, with the freshly cut posterior surface of the lenticle exposed for precision lathing to predetermined contour. After lathing and thawing, the lenticle is reapplied to the eye, and is then sutured in stroma-to-stroma contact with the cornea from which it was removed.

A keratomileusis procedure thus contemplates full preservation of the anterior surface of the cornea, and a lathe-sculpturing removal of stromal tissue only from the posterior surface of the severed lenticle. If the lathing is to a characterized predetermined depth of cut which is greatest at the optical axis and which reduces to zero at the outer radius of the optically used part of the cornea, then upon applying the lathed lenticle to the eye, a myopia-correcting result is obtained. If, on the other hand, the lathing depth of cut is greatest at the outer radius of the optically used part of the cornea, with reducing depth of cut as a function of reducing radius, then a hyperopia-correcting result is obtained.

We know of no reported efforts to apply laser surgery in any updated performance of a keratomileusis operation. However, Trokel, et al. in their paper entitled "Excimer Laser Surgery of the Cornea", Am. J. Ophthal. 96: 710–715, December 1983, do suggest the possibility of such an operation.

Meanwhile, various L'Esperance, Jr. patents have issued, describing use of tissue-ablating laser radiation, directed to the optically used central region of the anterior surface of the cornea, to effect optical correction by tissue-ablating action, with volumetric removal of corneal tissue. These patents illustratively include those numbered 4,665,913, 4,669,466, 4,732,148, 4,729,372, and 4,770,172, and their disclosures, as well as Dr. Girard's said Chapter 6, are hereby incorporated by reference.

BRIEF STATEMENT OF THE INVENTION

It is an object of the invention to provide a new and improved technique and apparatus for performing a keratomileusis or the like operation.

Another specific object is to provide a new and improved technique and apparatus for surgically modifying optical properties of an eye without surgically invading the central optically used region of the anterior surface of the cornea.

A specific object is to achieve the above objects through laser-ablating removal of only stromal tissue from the optically used central region of the cornea.

Another specific object is to provide a technique and apparatus for performing a keratomileusis operation without surgically invading any optically used part of the lenticle that is severed at commencement of the operation.

The invention achieves the foregoing objects by modifying conventional keratomileusis procedure to the extent that controlled tissue-ablating laser radiation is applied solely to the freshly cut part of the cornea that is left after severing the lenticle, the radiation being so controlled and characterized as to effect a volumetric removal of exclusively stromal tissue that, upon replacement of the lenticle over the thus-sculptured remainder of the cornea, a new and optically corrected curvature results.

DETAILED DESCRIPTION

The invention will be described in detail in conjunction with the accompanying drawings, in which.

Figures 1, 2:
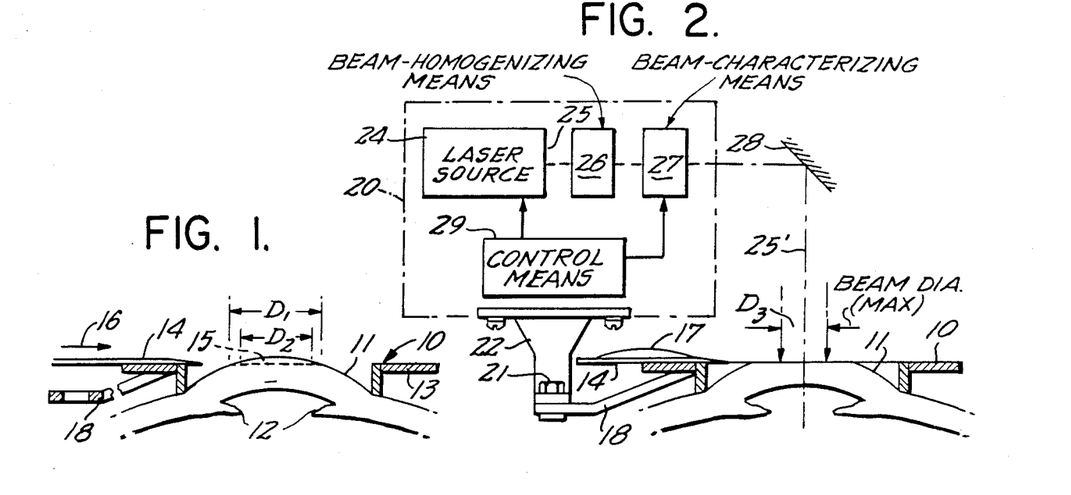
FIG. 1 is a simplified sectional view of a cornea, with annular eye-retaining and microtome structure in locating relation with the limbus of the cornea.
FIG. 2 is a schematic diagram of a laser and control means for operating upon the retained cornea of FIG. 1.

In FIG. 1, annular eye-retaining ring structure 10 is shown in locating engagement with a cornea 11 having a dilated iris 12, and said structure includes a flange 13 which establishes a horizontal plane of reference for the cutting blade 14 of a microtome. The central bulbous contour of the anterior surface of the cornea projects beyond this horizontal plane, and a dashed line 15 indicates the line of cornea-truncating cut by the microtome blade when guided by flange 13 in the direction of arrow 16, transverse to the optical axis of the eye. This truncating cut is at such maximum depth (on the axis of the eye) that a lenticle 17 (FIG. 2) is severed from the cornea, and the diameter $D_1$ of the lenticle (and thus also the freshly cut portion of the remaining body of the cornea) substantially exceeds the diameter $D_2$ of the optically used central area of the cornea. Preferably, the depth of this truncating cut is such that the cut area of diameter $D_2$ is entirely within stroma tissue of the cornea, i.e., it is beneath any involvement with Bowman's membrane in the area defined by diameter $D_2$. And a lateral stabilizing-arm part 18 of structure 10 is adapted for detachably fixed connection to laser apparatus 20 (FIG. 2).

The ring structure 10 and microtome blade 14 will be understood to have been simplified because precision equipment, designed by Dr. Barraquer for presently described purposes, exists and is commercially available, for example, as the Microkeratome Set marketed by Steinway Instrument Company, Inc., of San Diego, Calif. The Steinway Microkeratome Set is complete, with an assortment of eye-retaining rings 10 of various sizes, and with an assortment of plates (flange 13) for determining various depths of cut, as well as accessories to facilitate use for production of lenticle 17. The Steinway promotional bulletin, "Series I—The Barraquer Cryo-Lathe and Microkeratome Set", as well as Dr. Girard's said Chapter 6 provide detail as to the nature and use of the involved cutting apparatus, so that such detail is not needed in the present description.

Having made the cut which produced lenticle 17, it is preferred to retain a memory of the angular orientation of the lenticle with respect to the remaining body of the cornea. To this end, FIG. 2 shows lenticle 17 lying on the flat upper surface of blade 14, the same having been brought to this position by tweezer grasp of the leading edge of the lenticle as the lenticle is being cut, and by drawing this edge over the blade surface while making the cut, thus non-invasively setting aside and retaining the lenticle in known orientation with respect to the remaining body of the cornea from which it has been severed, so that the lenticle can later be placed in its correct original orientation with respect to said body. A drop of isotonic solution applied to the upper surface of blade 14, prior to making the cut, will facilitate this tweezer manipulation and also provides a degree of protection for the cut posterior surface of the lenticle.

The patient, who is preferably lying on his back, as related in said L'Esperance, Jr. patents, is now ready for correctly aligned positioning with respect to the laser apparatus 20, the same being secured via means 21 detachably connecting arm 18 to a bracket 22 or other fixture of the laser apparatus.

The apparatus 20 is schematically shown to include a laser source 24 producing an output beam 25 of radiation at a tissue-ablating intensity and wavelength, such as the pulsed 193 nm wavelength ultraviolet beam produced by an excimer laser operating with argon fluoride (ArF), all as described in commercial literature of Lambda-Physik, of Gottingen, West Germany and available in the United States from the Lambda-Physik facility in Acton, Mass.; refererence to and performance of a particular Lambda-Physik excimer laser is found in various L'Esperance, Jr. patents, including Pat. No. 4,665,913, and therefore no elaboration thereof is needed for purposes of the present description.

The apparatus 20 is further shown to include beam-homogenizing means 26, followed by beam-characterizing means 27, before folding at a mirror 28 for vertically downward delivery on axis 25' to the center of the stromal tissue exposed upon lenticle 17 removal. A dimensional indication at diameter $D_3$ illustrates the maximum cross section diameter of the beam at impact with cornea 11. For purposes of achieving a desired optical correction, this maximum diameter $D_3$ of laser-beam exposure to the cornea may be less than the maximum diameter $D_2$ accommodated by a dilated iris 12, as will later become clear.

Reference is made to pending Telfair, et al. application Ser. No. 009,724, filed Feb. 2, 1987, for detailed description of suitable beam-homogenizing means 26, and for present purposes it is sufficient to indicate that the action of means 26 is such as to provide an output of laser-beam delivery to the succeeding means 27 wherein the laser beam is of substantially uniform flux density over the sectional area of the thus-delivered beam. Reference is made to L'Esperance, Jr. Pat. No. 4,732,148, and to pending Yoder patent application Ser. No. 204,504, filed June 9, 1988 for descriptions of suitable beam-characterizing means 27; and it is sufficient to note for present purposes that beam delivery afforded by the disclosure of these latter references is of the variety wherein the size and shape of the laser-beam section is varied by suitable control means 29 in the course of a given laser-surgery exposure. Depending upon the shape which is thus dimensionally varied, the ablation of corneal tissue results in sculpture to a desired new profile of the exposed surface area, the diameter $D_3$ of which is illustratively 4 to 6 mm for myopia, hyperopia and/or astigmatism correction. We sometimes refer to the technique indicated for beam-characterizing by means 27 as the varying spot-size technique.

Figure 3:
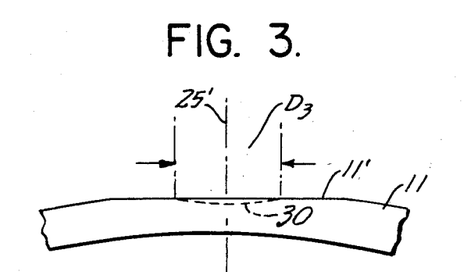
FIG. 3 is a sectional view of a cornea, to enlarged scale, in aid of discuss±on of curvature-decreasing optical corrections achievable in use of the invention.

FIG. 3 illustrates the important step of the invention, using the apparatus of FIG. 2 to perform a myopia-reducing laser-ablating sculpture of the central area (diameter $D_3$) within the freshly cut region 11' of the cornea, after microtome removal of lenticle 17. Within this central area, laser spot size is controlled by means 27, 29 to be a circle centered on the optical axis (beam axis 25'), and the diameter of the circle is caused to vary in the course of a predetermined ablation-producing exposure. Thus, if the diameter is near-zero at commencement of the exposure, and if the diameter expands in the course of the exposure, to the point of achieving diameter $D_3$ at the end of the exposure, the resulting curvature of depth penetration into the freshly cut region 11' is a concavity having a profile 30 of circular symmetry about axis 25'. And when lenticle 17 is thereafter returned into concentric registry and stroma-to-stroma contact with surface 11' (and its newly sculpted concavity 30), the net effect is a curvature reduction and thus a myopia-reducing change in the anterior-surface curvature of the cornea, it being noted that lenticle 17 is sufficiently pliant to retain its new curvature, as dictated by the stroma-to-stroma contact.

What has been said as to the spherical myopia-reducing change effected by the sculpture step of FIG. 3 can also be said for an astigmatism-reducing change, also illustrated by FIG. 3, if the sculpted curvature profile 30 is viewed as being the section of a cylindrical arc, which section extends diametrically across the area of diameter $D_3$. To produce such cylindrically arcuate sculpture, i.e., from surface 11' to the diametrically extending constant cylindrically arcuate contour 30, the controlled varying spot size of tissue-ablating radiation delivered on axis 25' is a diametrically extending line or stripe of varying width, which at beginning of the exposure may be most narrow, but which expands in width, and with lateral symmetry both sides of said diametrically extending line, in the course of the predetermined full exposure. If the angular orientation of the said diametrically extending line is set in accordance with the cylindrical axis of astigmatism to be corrected, then upon returning lenticle 17 into concentric registry and stroma-to-stroma contact with surface 11' (and its newly sculpted concavity 30), the net effect is a cylindrical curvature reduction in the anterior surface of the cornea, which curvature reduction is correctly oriented for astigmatism correction of the involved eye.

Figure 4:
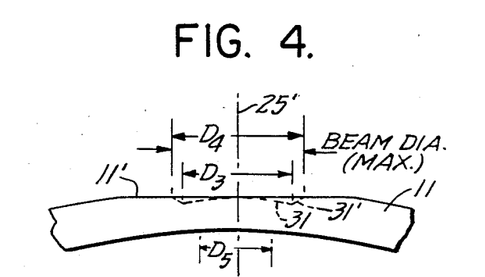
FIG. 4 is a view similar to FIG. 3, applicable to curvature-increasing optical corrections.

In a manner analogous to the spherical and/or cylindrical curvature reduction procedures described in connection with FIG. 3, FIG. 4 illustrates the case for curvature increase, to effect correction of a hyperopia condition. In FIG. 4, the laser-sculpted intrusion into the freshly cut surface 11' establishes a convex profile 31 of circular symmetry about axis 25', over the area (of diameter $D_3$) afforded by the maximum beam diameter used in the cases of FIG. 3, it being recalled that said maximum beam diameter had been selected to accord with the optically used area of the cornea to be surgically improved, i.e., not necessarily the maximum diameter $D_2$ afforded by a fully dilated iris 12. But to limit the hyperopia-correcting convex profile 31 to the diameter $D_3$ desired for optical correction is to present the disadvantage of not achieving hyperopia correction to the full desired extent of diameter $D_3$. This is because the convex profile 31 alone would mean a sharp outer circular edge of maximum depth penetration into the cut surface 11', and application of lenticle 17 to such a profile could degrade optical performance of the resulting anterior-surface profile, due to the difficulty of assuring full stroma-to-stroma seating of the lenticle on the sculpted surface 11', particularly at and near the outer circular locus of greatest ablated-depth penetration into surface 11'. To offset this difficulty, the profile 31 is flared or beveled, from maximum-depth penetration to zero penetration, in an annular zone 31' (of outer diameter $D_4$) contiguous to and radially outside the optically correcting convex profile 31. As explained in detail in L'Esperance, Jr. Pat. No. 4,732,148, the laser-sculpting production to the combined optically correcting and flaring profiles (31, 31') is obtained by such varying beam-section control by means 27, 29 as to project an annulus of laser beam impingement wherein the annulus is at all times during the exposure based on the circular locus of diameter $D_3$, and wherein the inner radius of the projected annulus varies progressively in the radially inward direction to the point of zero or near-zero exposure on axis 25', while at the same time the outer radius of the projected annulus varies progressively in the radially outward direction to the point of zero or near-zero exposure at diameter $D_4$. Having performed the profiling operation (31, 31') on the freshly cut surface 11', lenticle 17 is concentrically applied thereto with stroma-to-stroma contact over all cut and sculptured surfaces, whereby the anterior surface of the cornea pliantly assumes the desired new circumferentially beveled hyperopia-correcting curvature.

Figure 5:
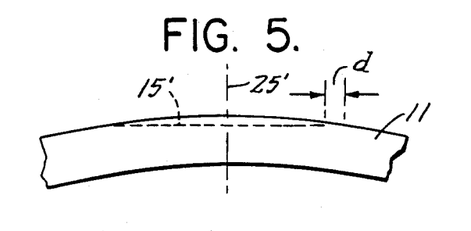
FIG. 5 is a sectional view of a cornea, to illustrate a modified technique of the invention.
Figure 6:
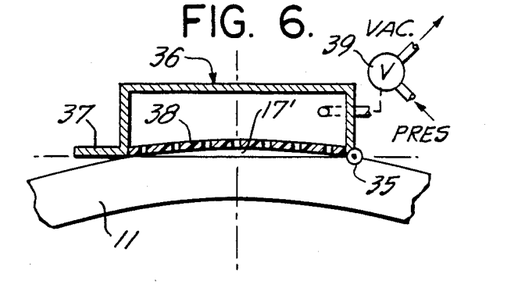
FIG. 6 is a sectional view of apparatus usable in performing the technique of FIG. 5, shown applied to the cornea of FIG. 5.
Figure 7:
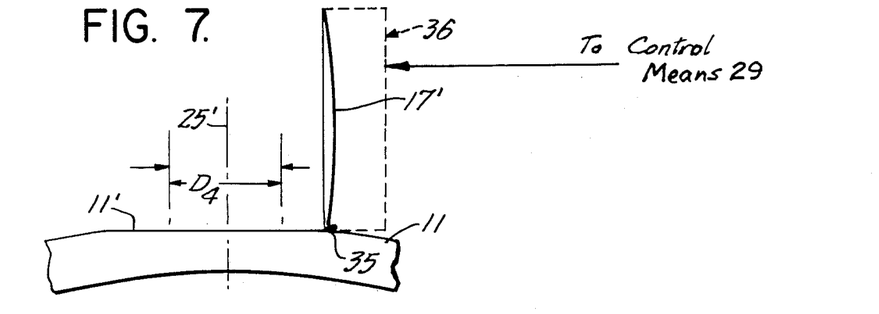
FIG. 7 is a simplified sectional diagram, to illustrate an articulated employment of apparatus of FIG. 6, in performing the technique of FIG. 5.

FIGS. 5, 6 and 7 are directed to a modification of technique and apparatus, whereby accuracy of registration and orientation can be assured upon lenticle replacement over the laser-ablated stroma at the freshly cut surface 11'. This is made possible by so making the microtome cut, on alignment 15' (FIG. 5), as to terminate a distance d short of totally severing the lenticle 17' from the rest of the cornea. The lenticle 17' is then treated as a hinged flap which can be engaged and articulated about a fixed axis 35 by the hinged holding device 36 shown in FIG. 6.

The holding device 36 comprises an inverted cup-shaped enclosure having a flange 37 for supporting engagement with the upper rim edge of the eye-retaining device 10. The otherwise-open bottom wall of the enclosure is closed by a perforated or foraminous wall 38 selected for contour compatability with the pre-surgery profile of the anterior surface of the patient's cornea. A valve 39 is selectively operable into three positions, in the first of which the interior volume or plenum of enclosure 36 is connected to a vacuum line, in the second of which the interior volume of enclosure 36 is connected to a source of air pressure, and in the third of which the vacuum and pressure-source connections are both cut off. The hinge designation 35 in FIG. 6 will be understood to suggest selectively removable hinging attachment of the holding device 36 to hinge-connection means 35' forming a part of the eye-retaining structure 10 of FIG. 2.

In use of the procedure and apparatus of FIGS. 5 to 7, a microtome cut is made on alignment 15', leaving a pliant hinge connection (of extent d) between the lenticle flap 17' and the remaining body of the cornea. The holding device 36 is then hinge-connected at 35-35' to the eye retainer 10, and the device 36 is lowered with the porous wall 38 in conforming relation to the anterior surface of the lenticle flap 17'. Valve 39 is then actuated to provide a vacuum connection to the inner plenum volume of device 36, whereupon the lenticle flap adheres to wall 38, and device 36 is elevated to its up position, shown by phantom outline in FIG. 7; in the raised position of FIG. 7, an arrow 36' is suggestive of position-certifying contact with the plenum structure 36, and means 29, whereby tissue-ablating laser radiation cannot be delivered unless the raised position of FIG. 7 has been certified to the control means. The cut surface 11' to be laser sculpted is then clearly exposed, centered on axis 25', for such corrective ablating surgery as has been illustratively described in connection with FIGS. 3 and 4. Upon completion of the surgical procedure, device 36 (and the lenticle flap it has been holding) is returned to its down position (FIG. 6) with the lenticle flap in precise register with its original relationship to the rest of the cornea, and further actuation of valve 39 from its vacuum connection to its air-pressure connection is operative not only to release the lenticle flap from wall 38 but also to apply gentle and well-distributed downward force loading of the lenticle flap in stroma-to-stroma contact with the now-sculptured surface 11'; in the process, the anterior surface of the lenticle flap becomes once more the anterior surface of the cornea, but with a newly corrected optically functioning curvature achieved by pliant adaptation to the sculptured profile.

It will be seen that the described procedures and apparatus achieve all stated objects, and it will be appreciated that the invention is not limited to particular wavelengths as long as the involved laser radiation is tissue-ablating, i.e., has the inherent ability to photochemically (in the ultraviolet), photo-thermally (in the infrared) or otherwise destroy tissue without leaving scar tissue in or adjacent to the region of laser-radiation exposure.

It is also to be understood that the invention is not limited to the myopia-correcting, hyperopia-correcting and astigmatism-correcting usages described in connection with FIGS. 3 and 4. For example, the near-vision capability of a hyperopic eye may be improved by making a curvature-increasing profile that is limited essentially to a relatively small central area (e.g., as suggested by dimension $D_5$ in FIG. 4), and by uniformly ablating the remaining annulus ($D_5$–$D_3$) of the visually used area of the cornea. More specifically, the curvature-increasing profile within dimension $D_5$ will involve greatest ablation-depth penetration ($d_{max}$) at diameter $D_5$, and by uniformly ablating the remaining annulus ($D_5$–$D_3$) to said maximum depth ($d_{max}$) one leaves the far-vision capability substantially untouched in the annulus ($D_5$–$D_3$). However, at the outer limit $D_3$ of this annulus, a sharp outer-wall contour may be produced, with degrading effect at diameter $D_3$ after the lenticle has been replaced; it is therefore again recommended, as in FIG. 4, that a bevel 31' be developed up to diameter $D_4$, in the outer annulus ($D_4$–$D_3$) which is not relied upon for optical use.

Also, by way of example, the near-vision capability and far-vision capability of a particular eye can be enhanced by effecting a first (and far-vision enhancing) curvature profile in the outer annulus ($D_3$–$D_5$) of the optically used area of the cornea and a second (and near-vision enhancing) curvature profile in the central circular area defined by the diameter $D_5$, with the respective curvature profiles being of circular symmetry about the optical axis and also smoothly continuous at their circle ($D_3$) of contiguous adjacency.

And a myopic eye may be given improved far-vision capability without destruction of its natural near-vision capability, provided the myopic error coincides with appropriate near-vision distance, by limiting the area of myopic correction to the area ($D_3$–$D_5$) outside the central optically used area $D_5$ of the cornea. This result is achieved by laser ablation of the outer surface 11' within the area ($D_5$–$D_3$) to a concave profile annulus similar in all other respects to profile 31 described in connection with FIG. 4, i.e., with tissue ablating exposure only within the annulus area ($D_5$–$D_3$) which would correct the myopic refractive error for distance. Various degrees of tissue-ablating exposure to the small central area (diameter $D_5$) would be necesssary only if the inherent myopic refractive error were greater or less than the appropriate distance for reading or other near-vision capability required by the patient's work. Again preferably, a bevel sculpture 31' up to diameter $D_4$, would be made in the annular area ($D_3$–$D_4$) not relied upon for optical use.

What is claimed is:

1. The method of changing optical properties of an eye by operating upon the cornea without invasion of the optically used central area of the anterior surface of the cornea, which method comprises surgically separating a lenticle from the anterior of the cornea at a circumferential intercept which is substantially concentric with the optical axis of the eye but which externally surrounds the optically used central area, thus exposing within said central area only stroma tissue of a remaining body of the cornea, the surgical separation of the lenticle being substantially in a single radial plane about the axis optical of the eye, and the separation being via a diametral cutting displacement which enters the cornea on one side of the axis optical of the eye and which fully traverses the optically used central area and terminates prior to completion of separation, whereby a relatively narrow flexible tissue connection exists between the lenticle and the remaining body of the cornea; hingedly removing the lenticle via articulation about said flexible connection; selectively applying tissue-ablating laser radiation to thus-exposed stroma tissue while the lenticle is thus removed, said tissue-ablating laser radiation being with depth penetration solely into stroma tissue and to a predetermined curvature profile; and, after laser-ablating exposure, replacing the lenticle via return articulation about said flexible connection, whereby fidelity of replaced-lenticle orientation is assured by said connection.

2. The method of changing optical properties of an eye by operating upon the cornea without invasion of the optically used central area of the anterior surface of the cornea, which method comprises surgically separating a lenticle from the anterior of the cornea at a circumferential intercept which is substantially concentric with the optical axis of the eye but which externally surrounds the optically used central area, thus exposing within said central area only stroma tissue of a remaining body of the cornea, non-invasively retaining the lenticle in known orientation with respect to the cornea from which it has been severed, so that the lenticle can later be replaced in its correct original orientation with respect to said body, selectively applying tissue-ablating laser radiation to thus-exposed stroma tissue with depth penetration solely into the stroma tissue and to a predetermined curvature profile, and thereafter replacing the lenticle in stroma-to-stroma contact with and in circumferential overlap of the thus profiled region of said body.

3. The method of claim 2 or claim 1, in which said predetermined curvature profile is of circular symmetry and is characterized by ablation-depth penetration which is greatest at the center and least at the outer limit of said optically used central area, whereby to effect a myopia-reducing curvature correction of the eye.

4. The method of claim 2 or claim 1, in which said predetermined curvature profile is of circular symmetry and is characterized by ablation-depth pentration which is least at the center and greatest at the outer limit of said optically used central area, whereby to effect a hyperopia-reducing curvature correction of the eye.

5. The method of claim 2 or claim 1, in which said predetermined curvature profile is of circular symmetry and is characterized by ablation-depth penetration whioh is least at the center and greatest at the outer limit of said optically used central area, whereby to effect a hyperopia-reducing curvature correction of the eye, there being an annulus of exposed stroma tissue surrounding the outer limit of said optically used central area, and tissue-ablating laser radiation being applied within said annulus and with depth penetration in stroma tissue to a curvature profile which is continuous with said predetermined profile at the inner limit of said annulus and which reduces to substantially zero depth penetration at the outer limit of said annulus.

6. The method of claim 2 or claim 1, in which said predetermined curvature profile is of lateral symmetry on opposite sides of a diametral alignment through said optically used central area, the orientation of said alignment being selected for correction of a diagnosed astigmatic condition of the eye.

7. The method of claim 2 or claim 1, in which said predetermined curvature profile is in an outer circular annulus concentric with the optical axis and within the optically used central area of said exposed body-stroma tissue, the predetermined curvature profile being of circular symmetry centered on the optical axis and characterized by ablation-depth penetration which is least at the inner radial limit of said annulus and greatest at the outer limit of said optically used area, whereby to improve the far-vision capability of a myopic eye.

8. The method of claim 2 or claim 1, in which said predetermined curvature profile is an outer circular annulus concentric with the optical axis and within the optically used central area of said exposed stroma tissue of the remaining body, the predetermined curvature profile being of circular symmetry centered on the optical axis and characterized by ablation-depth penetration which is least at the inner radial limit of said annulus and greatest at the outer limit of said optically used area, whereby to improve the far-vision capability of a myopic eye, there being a second annulus of exposed stroma tissue surrounding the outer limit of said optically used central area, and tissue-ablating laser radiation being applied within said second annulus and with depth penetration in stroma tissue to a curvature profile at the inner limit of said second annulus, said penetration reducing to substantially zero depth the outer limit of said second annulus.

9. The method of claim 2 or claim 1, in which said predetermined curvature profile is to a first curvature in an outer annular area concentric with the optical axis and within the optically used central area of said exposed body-stroma tissue and to a second curvature in the inner area that is contiguous to and surrounded by said annular area, both curvatures (1) being of circular symmetry centered on the optical axis and (2) being characterized by ablation-depth penetration which increases with increasing radial offset from said axis, the depth-penetration increase per unit radial-offset increase in said inner area exceeding the depth-penetration increase per unit radial-offset increase in said outer area.

10. The method of claim 2 or claim 1, in which the tissue-ablating laser radiation is in the ultra-violet wavelength region of the spectrum, for photo-chemical ablation of involved stroma tissue.

11. The method of claim 2 or claim 1, in which the tissue-ablating laser radiation is in the infrared wavelength region of the spectrum, for photo-thermal ablation of involved stroma tissue.

12. Apparatus for changing optical properties of an eye by effecting a curvature correction in the optically used central area of the cornea, said apparatus comprising microtome means including an annular base adapted for seating reference to the cornea at a region outside said optically used area and generally concentric therewith, said microtome means including guide means for a blade adapted to surgically cut a lenticle from the anterior surface of the cornea at a circumferential intercept which is substantially concentric with the optical axis of the eye and which externally surrounds the optically used central area, a lenticle-supporting device having articulated connection to said base for selectively engaging, supporting and transporting a severed lenticle to a removed position out of a cylindrical path normal to the optically used central area and of cross-section at least equal to said central area, and laser means connected to said base and projecting a tissue-ablating beam on said path to said area, said laser means including control means for selectively delivering tissue-ablating laser radiation to stroma tissue within said area only when said supporting device has removed the lenticle from said path, said laser radiation impacting stroma tissue in a program of tissue ablation with depth penetration to a predetermined curvature profile, and means for operating said supporting means to transport the severed lenticle back into registration and overlap with said area upon completion of said program.

13. The apparatus of claim 12, in which said lenticle-supporting device has a foraminated concave lenticle-engaging front member, and a plenum covering the back side of said member; and selectively operable means for selective imposition of a vacuum or of a pressurized gas condition within said plenum.

* * * * *

(12) REEXAMINATION CERTIFICATE (4438th)
United States Patent
Warner et al.

(10) Number: US 4,903,695 C1
(45) Certificate Issued: Sep. 11, 2001

(54) METHOD AND APPARATUS FOR PERFORMING A KERATOMILEUSIS OR THE LIKE OPERATION

(75) Inventors: John W. Warner, Newtown, CT (US); Francis A. L'Esperance, Jr., Englewood, NJ (US)

(73) Assignee: LRI L.P., New York, NY (US)

Reexamination Requests:
No. 90/004,888, Jan. 9, 1998
No. 90/005,706, Apr. 14, 2000

Reexamination Certificate for:
Patent No.: 4,903,695
Issued: Feb. 27, 1990
Appl. No.: 07/278,272
Filed: Nov. 30, 1988

(51) Int. Cl.$^7$ ............................................. A61B 9/01
(52) U.S. Cl. ..................... 606/4; 606/3; 606/5; 606/11; 606/12; 606/18
(58) Field of Search ...................... 606/3.5, 10–13, 606/17, 18

(56) References Cited

U.S. PATENT DOCUMENTS

| | | | |
|---|---|---|---|
| 3,982,541 | * | 9/1976 | L'Esperance, Jr. ................. 606/4 |
| 4,122,853 | * | 10/1978 | Smith ................................ 606/4 |
| 4,425,235 | | 1/1984 | Cornell et al. . |
| 4,583,539 | * | 4/1986 | Karlin et al. ...................... 606/4 |
| 4,676,790 | | 6/1987 | Kern . |
| 4,729,372 | * | 3/1988 | L'Esperance, Jr. ................. 606/5 |
| 4,732,148 | * | 3/1988 | L'Esperance, Jr. ................. 606/5 |
| 4,840,175 | | 6/1989 | Peyman . |
| 5,108,388 | * | 4/1992 | Trokel .............................. 606/5 |
| 5,219,344 | * | 6/1993 | Yoder, Jr. ......................... 606/5 |
| 5,624,452 | | 4/1997 | HellenKamp . |
| 5,658,303 | | 8/1997 | Koeprick . |
| 5,807,380 | | 9/1998 | Dishler . |
| 5,980,543 | | 11/1999 | Carriazo . |

OTHER PUBLICATIONS

Testimony of Richard H. Keates in *In re Summit Tech., Inc. et al.*, No. 9286 (F.T.C.).
Testimony of Stephen L. Trokel in *In re Summit Tech., Inc. et al.*, No. 9286 (F.T.C.).
Expert report of Neal A. Sher, M.D., dated Nov. 2, 1998.
Expert report of Neal A. Sher, M.D., dated Nov. 13, 1998 (different content).
Expert report of Massoud Motamedi, Ph.D., dated Nov. 2, 1998.
George O. Waring III, *Development & Eval. of Refractive Surgical Procedures* (1987).

(List continued on next page.)

*Primary Examiner*—Lee S. Cohen (57) ABSTRACT

A conventional keratomileusis procedure is modified to the extent that a controlled tissue-ablating laser radiation is applied solely to the freshly cut part of the cornea that is left after severing the lenticle, the radiation being so controlled and characterized as to effect a volumetric removal of exclusively stromal tissue that, upon replacement of the lenticle over the thus-sculptured remainder of the cornea, a new and optically corrected curvature results.

OTHER PUBLICATIONS

Draft article with editor's notes, Stephen L. Trokel et al., *Excimer Laser Surgery of the Cornea*.
Copy of YAG Laser Ophthalmic Microsurgery, edited by Stephen L. Trokel, M.D., copywrite 1983 by Appleton–Century–Crofts.
Excimer Lasers in Ophthalmology® Martin Dunitz Ltd 1997 pp. 295–317 Exhibit 19.
LASIK Surgical Techniques and Complications, SLACK, Inc. Copyright 2000, pp. 3–14 and 248 Exhibit 20.
Ophthalmology Times, p. 35, Jun. 1, 1994 Exhibit 21.
Ophthalmology Times, p. 6, Jan. 1, 1998 Exhibit 22.
Ophthalmology Times, p. 15, Jun. 15, 1998 Exhibit 23.
Ophthalmology Times, p. 14, May 15, 1997 Exhibit 24.
Ophthalmology Times, p. 6, Nov. 15, 1997 Exhibit 25.
Ophthalmology Times, p. 23, Feb. 1, 1997 Exhibit 26.
Ophthalmology Times, p. 4, Jun. 1, 1996 Exhibit 27.
Executive Laser Briefing, Jan. 29, 1999, pp. 1, 14, and 15 Exhibit 28.
Ophthalmology Times, pp. 18–19, Mar. 1, 2000 Exhibit 29.
Ophthalmology Times, p. 34, Mar. 1, 2000 Exhibit 34.
Ophthalmology Times, p. 29, Nov. 1, 1997. Exhibit 35.
Ophthalmology Times, p. 14, Jul. 15, 1998 Exhibit 36.
Ophthalmology Times, p. 32, Nov. 15, 1996 Exhibit 38.
Ophthalmology Times, p. 53, May 15, 1999 Exhibit 39.
Krwawicz, *Lamellar Corneal Stromectomy*, 57 Am. J. Ophthalmology 28 (1964), pp. 828–833.
Barraquer, *Keratomileusis*, Internationl Surgery, Aug. 1967, pp. 103–117.
Girard, *Advanced Techniques in Ophthalmic Microsurgery*, The C. V. Mosby Company; St. Louis (1981), pp. 143–158.
Front Pages of 20 District Court Cases Involving the Subject Patent.
Amended Answer and Counter Claim in Pillar Point Partners et al. V. Dishler et al.
Complaint in the Mater of Summit Technology, Inc. and Visx, Inc.
Amended Complaint in Taboada V. Trokel et al.
Amended Answer in Pillar Point Partners et al. V. Dulaney et al.
"Basis of Refractive Keratoplasty" by Barraquer, Arch. Soc. Offal. Optom (1967), pp. 21–68, except for pp. 22 and 42.
"Lesion Duration and Curvature change in the Cornea Following Exposure to a Carbon Dioxide Laser," Mikesell et al. Report SAM–TR–79–26 (1979).
DE 3148748 A1 (German patent publication to Karp) (twelve pages).
English language translation of DE31 48 748 A1 to Karp (ten pages).
"Reshaping the Cat Corneal Anterior Surface Using a High–speed Diamond Fraise," Olson et al., (1980) (three pages). Ophthalmic Surgery Nov. 1980, vol. 11, No. 11, pp. 784–786.
"Basis of Refractive Keratoplasty"; Barraguer; Arch Soc Ophthal. optom; 1967, 21–41 & 43–68.*
Barraquer "Keratomileusis for Myopia and Aphakia"; Ophthalmology; vol. 88, No. 8;, Aug. 1981, pp. 701–708.*
Couderc et al "[Comparative Results of Myopia Keratomuleusis with and without Freezing](FR)" 53$^{rd}$ Congress of the French Society of Ophthalmogoy; Ophlalmogie; 1988; 2, 293–6*
Bosc et al "[Non–Freezing myopia keratomileusis; Results of 27 consecutive operatives](FR)"; Bull. Soc. Opht. France; 1990; vol. 1, pp. 77–86.*

Sledman's Medical Dictionary, 26$^{th}$ Ed. 1995; Williams & Wilkens; p. 152, 1300, 1529.*
American Heritage Dictionary 2$^{nd}$ Ed. 1982; Houghton Mifflin Co. pp. 613, 831.*
Jose I. Barraquer, "Basis of Refractive Keratoplasty", Jun. 21, 1967, pp. 21, 23–41 and 43–68.
Barraquer J, queratomileusis y Queratofaquia (Instituto Barraquer de America: Bogata, 1980) 79.*
Pureskin N, Weakening ocular refraction by means of partial stromectomy under experimental conditions, Vestnik Oftalmologii (1967) 80:1–7.*
TIME, pp. 60–66, Oct. 11, 1999 Exhibit 40.
Jobson's Review of Ophthalmology, Feb. 2000, pp. 39, 40, 45, and 46 Exhibit 41.
Executive Summary, Survey of Refractive Surgeons, Aug. 15, 1999, pp. 1–12 Exhibit 42.
Survey of Refractive Surgeon, Aug. 1999, pp. 1–6 Exhibit 43.
American Journal of Ophthalmology, Feb. 1999, pp. 202–204 Exhibit 44.
American Journal of Ophthalmology, Feb. 1999, pp. 129–136 Exhibit 45.
J. Cataract Refract Surg. Vol. 24, Jul. 1998, pp. 989–1006 Exhibit 46.
Yahoo! Finance copyright 2000 download Mar. 2, 2000 Exhibit 47.
Small Cap Report Feb. 19, 1999, pp. 1–3 Exhibit 48.
American Way, Feb. 1, 1999, pp. 76 and 78–80 Exhibit 49.
Fortune, Sep. 27, 1999, pp. 195, 196, 197, 200, and 207 Exhibit 50.
Health and Fitness, Oct. 12, 1999, pp. 3D and 4D Exhibit 51.
Moderne Möglich–keiten der mikro–chirurgischen Korrektur der Fehlsichtigkeit (English abstract) 1997 pp. 207–211 Exhibit 52.
Lessening of Eye Refraction by Partial Stromectomy of the Cornea Under Experimental Conditions, Pureskin, Oct. 1966, pp. 1–7; (English translation) Exhibit 53.
Barraquer J. Queratomileusis y Queratofaquia (Instituto Barraquer de America; Bogota, 1980) 79; (English translation) Exhibit 54.
Laser in Situ Keratomileusis, Pallikaris, Lasers in Surgery and Medicine, 1990, 10, pp. 463–468 Exhibit 55.
Wilmer Ophthalmological Institute Current Concepts in Ophthalmology, Refractive Surgery Update, Taylor, Dec. 2000, 2 pages Exhibit 56.
Letter to Freddie Park from David Harmon of Market Scope dated Feb. 2, 2001 Exhibit 57.
Excimer Lasers in Ophthalmology, Principles and Practices, Martin Dunitz Ltd, pp. 43–49, 1997 Exhibit 58.
Curriculum Vitae: Neal A. Sher, M.D., F.A.C.S.
Histopathological Comparison of Photorefractive Keratectomy and Laser In Situ Keratomileusis in Rabbits.
Laser Assisted in Situ Keratomileusis for high Myopia.
LASIK for high Myopia: One Year Experience.
Comparison of Laser in situ Keratomileusis and Photorefractive Keratectomy to Correct myopia from −1.25 to −6.00 Diopters.
Comparison of Laser situ Keratomileusis and Automated Lamellar Keratoplasty for the Treatment of Myopia.
Excimer Laser in Situ Keratomileusis to Correct Compound myopic Astigmatism.
Laser in situ Keratomileusis for Myopia of −2 to −25 Diopters.

Laser in situ Keratomileusis for Myopia of −1 to 3.50 Diopters.
Laser in situ keratomileusis to correct high mypoia.
Laser in situ Keratomileusis for Simple Myopic, Mixed, and Simple Hyperopic Astigmatism.
Laser in situ Keratomileusis for Myopia from −5 to −11.50 Diopters with Astigmatism.
Comparison of corneal sensation following protorefractive keratectomy and laser in situ keratomileusis.

Laser in situ keratomileusis for hyperopia.
Contrast sensitivity after laser in situ keratomileusis.
Lasers In–Situ Keratomileusis.
Lasers in Ophthalmology.
Laser refractive surgery: a review and current status.
Excimer Laser Protorefractive Keratectomy.

* cited by examiner

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1, 12, and 13 is confirmed.

Claims 2-11 are determined to be patentable as amended.

New claims 14-53 are added and determined to be patentable.

2. The method of changing optical properties of an eye by operating upon the cornea without invasion of the optically used central area of the anterior surface of the cornea, which method comprises *completely* surgically separating a lenticle from the anterior of the cornea at a circumferential intercept which is substantially concentric with the optical axis of the eye but which externally surrounds the optically used central area, thus exposing within said central area only stroma tissue of a remaining body of the cornea, non-invasively retaining the lenticle in known orientation with respect to the cornea from which it has been severed, so that the lenticle can later be replaced in its correct original orientation with respect to said body, selectively applying tissue-ablating laser radiation to thus-exposed stroma tissue with depth penetration solely into the stroma tissue and to a predetermined curvature profile, and thereafter replacing the lenticle in stroma-to-stroma contact with and in circumferential overlap of the thus profiled region of said body.

3. The method of claim 2 [or claim 1], in which said predetermined curvature profile is of circular symmetry and is characterized by ablation-depth penetration which is greatest at the center and least at the outer limit of said optically used central area, whereby to effect a myopia-reducing curvature correction of the eye.

4. The method of claim 2 [or claim 1], in which said predetermined curvature profile is of circular symmetry and is characterized by ablation-depth penetration which is least at the center and greatest at the outer limit of said optically used central area, whereby to effect a hyperopia-reducing curvature correction of the eye.

5. The method of claim 2 [or claim 1], in which said predetermined curvature profile is of circular symmetry and is characterized by ablation-depth penetration which is least at the center and greatest at the outer limit of said optically used central area, whereby to effect a hyperopia-reducing curvature correction of the eye, there being an annulus of exposed stroma tissue surrounding the outer limit of said optically used central area, and tissue-ablating laser radiation being applied within said annulus and with depth penetration in stroma tissue to a curvature profile which is continuous with said predetermined profile at the inner limit of said annulus and which reduces to substantially zero depth penetration at the outer limit of said annulus.

6. The method of claim 2 [or claim 1], in which said predetermined curvature profile is of lateral symmetry on opposite sides of a diametral alignment through said optically used central area, the orientation of said alignment being selected for correction of a diagnosed astigmatic condition of the eye.

7. The method of claim 2 [or claim 1], in which said predetermined curvature profile is in an outer circular annulus concentric with the optical axis and within the optically used central area of said exposed body-stroma tissue, the predetermined curvature profile being of circular symmetry centered on the optical axis and characterized by ablation-depth penetration which is least at the inner radial limit of said annulus and greatest at the outer limit of said optically used area, whereby to improve the far-vision capability of a myopic eye.

8. The method of claim 2 [or claim 1], in which said predetermined curvature profile is an outer circular annulus concentric with the optical axis and within the optically used central area of said exposed stroma tissue of the remaining body, the predetermined curvature profile being of circular symmetry centered on the optical axis and characterized by ablation-depth penetration which is least at the inner radial limit of said annulus and greatest at the outer limit of said optically used area, whereby to improve the far-vision capability of a myopic eye, there being a second annulus of exposed stroma tissue surrounding the outer limit of said optically used central area, and tissue-ablating laser radiation being applied within said second annulus and with depth penetration in stroma tissue to a curvature profile at the inner limit of said second annulus, said penetration reducing to substantially zero depth the outer limit of said second annulus.

9. The method of claim 2 [or claim 1], in which said predetermined curvature profile is to a first curvature in an outer annular area concentric with the optical axis and within the optically used central area of said exposed body-stroma tissue and to a second curvature in the inner area that is contiguous to and surrounded by said annular area, both curvatures (1) being of circular symmetry centered on the optical axis and (2) being characterized by ablation-depth penetration which increases with increasing radial offset from said axis, the depth-penetration increase per unit radial-offset increase in said inner area exceeding the depth-penetration increase per unit radial-offset increase in said outer area.

10. The method of claim 2 [or claim 1], in which the tissue-ablating laser radiation is in the ultra-violet wavelength region of the spectrum, for photo-chemical ablation of involved stroma tissue.

11. The method of claim 2 [or claim 1], in which the tissue-ablating laser radiation is in the infrared wavelength region of the spectrum, for photo-thermal ablation of involved stroma tissue.

*14. The method of claim 1, in which said predetermined curvature profile is of circular symmetry and is characterized by ablation-depth penetration which is greatest at the center and least at the outer limit of said optically used central area, whereby to effect a myopia-reducing curvature correction of the eye.*

*15. The method of claim 1, in which said predetermined curvature profile is of circular symmetry and is characterized by ablation-depth penetration which is least at the center and greatest at the outer limit of said optically used central area, whereby to effect a hyperopia-reducing curvature correction of the eye.*

*16. The method of claim 1, in which said predetermined curvature profile is of circular symmetry and is characterized by ablation-depth penetration which is least at the center and greatest at the outer limit of said optically used* central area, whereby to effect a hyperopia-reducing curvature correction of the eye, there being an annulus of exposed stroma tissue surrounding the outer limit of said optically used central area, and tissue-ablating laser radiation being applied within said annulus and with depth penetration in stroma tissue to a curvature profile which is continuous with said predetermined profile at the inner limit of said annulus and which reduces to substantially zero depth penetration at the outer limit of said annulus.

17. The method of claim 1, in which said predetermined curvature profile is of lateral symmetry on opposite sides of a diametral alignment through said optically used central area, the orientation of said alignment being selected for correction of a diagnosed astigmatic condition of the eye.

18. The method of claim 1, in which said predetermined curvature profile is in an outer circular annulus concentric with the optical axis and within the optically used central area of said exposed body-stroma tissue, the predetermined curvature profile being of circular symmetry centered on the optical axis and characterized by ablation-depth penetration which is least at the inner radial limit of said annulus and greatest at the outer limit of said optically used area, whereby to improve the far-vision capability of a myopic eye.

19. The method of claim 1, in which said predetermined curvature profile is an outer circular annulus concentric with the optical axis and within the optically used central area of said exposed stroma tissue of the remaining body, the predetermined curvature profile being of circular symmetry centered on the optical axis and characterized by ablation-depth penetration which is least at the inner radial limit of said annulus and greatest at the outer limit of said optically used area, whereby to improve the far-vision capability of a myopic eye, there being a second annulus of exposed stroma tissue surrounding the outer limit of said optically used central area, and tissue-ablating laser radiation being applied within said second annulus and with depth penetration in stroma tissue to a curvature profile at the inner limit of said second annulus, said penetration reducing to substantially zero depth the outer limit of said second annulus.

20. The method of claim 1, in which said predetermined curvature profile is to a first curvature in an outer annular area concentric with the optical axis and within the optically used central area of said exposed body-stroma tissue and to a second curvature in the inner area that is contiguous to and surrounded by said annular area, both curvatures (1) being of circular symmetry centered on the optical axis and (2) being characterized by ablation-depth penetration which increases with increasing radial offset from said axis, the depth-penetration increase per unit radial-offset increase in said inner area exceeding the depth-penetration increase per unit radial-offset increase in said outer area.

21. The method of claim 1, in which the tissue-ablating laser radiation is in the ultra-violet wavelength region of the spectrum, for photo-chemical ablation of involved stroma tissue.

22. The method of claim 1, in which the tissue-ablating laser radiation is in the infrared wavelength region of the spectrum, for photo-thermal ablation of involved stroma tissue.

23. The method of changing optical properties of an eye by operating upon the cornea without invasion of the optically used central area of the anterior surface of the cornea, which method comprises surgically separating a lenticle from the anterior of the cornea at a circumferential intercept which is substantially concentric with the optical axis of the eye but which externally surrounds the optically used central area, thus exposing within said central area only stroma tissue of a remaining body of the cornea, the surgical separation of the lenticle being substantially in a single radial plane about the axis optical of the eye, and the separation consisting of a diametral cutting displacement which enters the cornea on one side of the axis optical of the eye and which fully traverses the optically used central area and terminates prior to completion of separation, whereby a relatively narrow flexible tissue connection exists between the lenticle and the remaining body of the cornea; hingedly removing the lenticle via articulation about said flexible connection; selectively applying tissue-ablating laser radiation to thus-exposed stroma tissue while the lenticle is thus removed, said tissue-ablating laser radiation being with depth penetration solely into stroma tissue and to a predetermined curvature profile; and, after laser-ablating exposure, replacing the lenticle via return articulation about said flexible connection, whereby fidelity of replaced-lenticle orientation is assured by said connection.

24. The method of claim 23, in which said predetermined curvature profile is of circular symmetry and is characterized by ablation-depth penetration which is greatest at the center and least at the outer limit of said optically used central area, whereby to effect a myopia-reducing curvature correction of the eye.

25. The method of claim 23, in which said predetermined curvature profile is of circular symmetry and is characterized by ablation-depth penetration which is least at the center and greatest at the outer limit of said optically used central area, whereby to effect a hyperopia-reducing curvature correction of the eye.

26. The method of claim 23, in which said predetermined curvature profile is of circular symmetry and is characterized by ablation-depth penetration which is least at the center and greatest at the outer limit of said optically used central area, whereby to effeca hyperopia-reducing curvature correction of the eye, there being an annulus of exposed stroma tissue surrounding the outer limit of said optically used central area, and tissue-ablating laser radiation being applied within said annulus and with depth penetration in stroma tissue to a curvature profile which is continuous with said predetermined profile at the inner limit of said annulus and which reduces to substantially zero depth penetration at the outer limit of said annulus.

27. The method of claim 23, in which said predetermined curvature profile is of lateral symmetry on opposite sides of a diametral alignment through said optically used central area, the orientation of said alignment being selected for correction of a diagnosed astigmatic condition of the eye.

28. The method of claim 23, in which said predetermined curvature profile is in an outer circular annulus concentric with the optical axis and within the optically used central area of said exposed body-stroma tissue, the predetermined curvature profile being of circular symmetry centered on the optical axis and characterized by ablation-depth penetration which is least at the inner radial limit of said annulus and greatest at the outer limit of said optically used area, whereby to improve the far-vision capability of a myopic eye.

29. The method of claim 23, in which said predetermined curvature profile is an outer circular annulus concentric with the optical axis and within the optically used central area of said exposed stroma tissue of the remaining body, the predetermined curvature profile being of circular symmetry centered on the optical axis and characterized by ablation-depth penetration which is least at the inner radial limit of said annulus and greatest at the outer limit of said optically used area, whereby to improve the far-vision capability of a myopic eye, there being a second annulus of exposed stroms tissue surrounding the outer limit of said optically used central area, and tissue-ablating laser radiation being applied within said second annulus and with depth penetration in stroma tissue to a curvature profile at the inner limit of said second annulus, said penetration reducing to substantially zero depth the outer limit of said second annulus.

30. The method of claim 23, in which said predetermined curvature profile is to a first curvature in an outer annular area concentric with the optical axis and within the optically used central area of said exposed body-stroma tissue and to a second curature in the inner area that is contiguous to and surrounded by said annular area, both curvatures (1) being of circular symmetry centered on the optical axis and (2) being characterized by ablation-depth penetration which increases with increasing radial offset from said axis, the depth-penetration increase per unit radial-offset increase in said inner area exceeding the depth-penetration increase per unit radial-offset increase in said outer area.

31. The method of claim 23, in which the tissue-ablating laser radiation is in the ultra-violet wavelength region of the spectrum, for photo-chemical ablation of involved stroma tissue.

32. The method of claim 23, in which the tissue-ablating laser radiation is in the infrared wavelength region of the spectrum, for photo-thermal ablation of involved stroma tissue.

33. The method of changing optical properties of an eye by operating upon the cornea without invasion of the optically used central area of the anterior surface of the cornea, which method consists of surgically separating a lenticle from the anterior of the cornea at a circumferential intercept which is substantially concentric with the optical axis of the eye but which externally surrounds the optically used central area, thus exposing within said central area only stroma tissue of a remaining body of the cornea, the surgical separation of the lenticle being substantially in a single radial plane about the axis optical of the eye, and the separation being via a diametral cutting displacement which enters the cornea on one side of the axis optical of the eye and which traverses the optically used central area and terminates prior to completion of separation, whereby a relatively narrow flexible tissue connection exists between the lenticle and the remaining body of the cornea; hingedly removing the lenticle via articulation about said flexible connection; selectively applying tissue-ablating laser radiation to thus-exposed stroma tissue while the lenticle is thus removed, said tissue-ablating laser radiation being with depth penetration solely into stroma tissue and to a predetermined curvature profile; and, after laser-ablating exposure, replacing the lenticle via return articulation about said flexible connection, whereby fidelity of replaced-lenticle orientation is assured by said connection.

34. The method of claim 33, in which said predetermined curvature profile is of circular symmetry and is characterized by ablation-depth penetration which is greatest at the center and least at the outer limit of said optically used central area, whereby to effect a myopia-reducing curvature correction of the eye.

35. The method of claim 33, in which said predetermined curvature profile is of circular symmetry and is characterized by ablation-depth penetration which is least at the center and greatest at the outer limit of said optically used central area, whereby to effect a hyperopia-reducing curvature correction of the eye.

36. The method of claim 33, in which said predetermined curvature profile is of circular symmetry and is characterized by ablation-depth penetration which is least at the center and greatest at the outer limit of said optically used central area, whereby to effect a hyperopia-reducing curvature correction of the eye, there being an annulus of exposed stroma tissue surrounding the outer limit of said optically used central area, and tissue-ablating laser radiation being applied within said annulus and with depth penetration in stroma tissue to a curvature profile which is continuous with said predetermined profile at the inner limit of said annulus and which reduces to substantially zero depth penetration at the outer limit of said annulus.

37. The method of claim 33, in which said predetermined curvature profile is of lateral symmetry on opposite sides of a diametral alignment through said optically used central area, the orientation of said alignment being selected for correction of a diagnosed astigmatic condition of the eye.

38. The method of claim 33, in which said predetermined curvature profile is in an outer circular annulus concentric with the optical axis and within the optically used central are of said exposed body-stroma tissue, the predetermined curvature profile being of circular symmetry centered on the optical axis and characterized by ablation-depth penetration which is least at the inner radial limit of said annulus and greatest at the outer limit of said optically used area, whereby to improve the far-vision capability of a myopic eye.

39. The method of claim 33, in which said predetermined curvature profile is an outer circular annulus concentric with the optical axis and within the optically used central area of said exposed stroma tissue of the remaining body, the predetermined curvature profile being of circular symmetry centered on the optical axis and characterized by ablation-depth penetration which is least at the inner radial limit of said annulus and greatest at the outer limit of said optically used area, whereby to improve the far-vision capability of a myopic eye, there being a second annulus of exposed stroma tissue surrounding the outer limit of said optically used central area, and tissue-ablating laser radiation being applied within said second annulus and with depth penetration in stroma tissue to a curvature profile at the inner limit of said second annulus, said penetration reducing to substantially zero depth the outer limit of said second annulus.

40. The method of claim 33, in which said predetermined curvature profile is to a first curvature in an outer annular area concentric with the optical axis and within the optically used central area of said exposed body-stroma tissue and to a second curvature in the inner area that is contiguous to and surrounded by said annular area, both curvatures (1) being of circular symmetry centered on the optical axis and (2) being characterized by ablation-depth penetration which increases with increasing radial offset from said axis, the depth-penetration increase per unit radial-offset increase in said inner area exceeding the depth-penetration increase per unit radial-offset increase in said outer area.

41. The method of claim 33, in which the tissue-ablating laser radiation is in the ultra-violet wavelength region of the spectrum, for photo-chemical ablation of involved stroma tissue.

42. The method of calim 33, in which the tissue-ablating laser radiation is in the infrared wavelength region of the spectrum, for photo-thermal ablation of involved stroma tissue.

43. The method of changing optical properties of an eye by operating upon the cornea without invasion of the optically used central area of the anterior surface of the cornea, which method comprises:

surgically separating a lenticle from the anterior of the cornea at a circumferential intercept which is substantially concentric with the optical axis of the eye but which externally surrounds the optically used central area, thus exposing within said central area only stroma tissue of a remaining body of the cornea, the surgical separation of the lenticle being substantially in a single radial plane about the axis optical of the eye, and the separation being via a diametral cutting displacement which enters the cornea on one side of the axis optical of the eye and which fully traverses the optically used central area and terminates prior to completion of separation, whereby a relatively narrow flexible tissue connection exists between the lenticle and the remaining body of the cornea, said relatively narrow tissue connection being sufficient to provide to said tissue connection a hinging function such that (1) the lenticle can be rotated around said tissue connection from an initial position adjacent the anterior of the cornea to be displaced position in which the lenticle would be out of any path that both (a) intercepts any portion of the optically used central area and (b) is perpendicular to said circumferential intercept and (2) the lenticle can be rotated from said displaced position back to said initial position such that accuracy of registration and orientation can be assured upon lenticle replacement over said central area:

hingedly removing the lenticle away from said optically used central area via articulation about sid flexible tissue connection;

selectively applying tissue-ablating laser radiation to thus-exposed stroma tissue while the lenticle is thus removed, said tissue-ablating laser radiation being with depth penetration solely into stroma tissue and to provide a resulting stroma surface having a predetermined curvature profile; and, after laser-ablating exposure, replacing the lenticle via return articulation about said flexible tissue connection in precise register with an original relationship of said lenticle to the rest of the cornea, whereby fidelity of replaced-lenticle orientation is assured by said connection.

44. The method of claim 43, in which said predetermined curvature profile is of circular symmetry and is characterized by ablation-depth penteration which is greatest at the center and least at the outer limit of said optically used central area, whereby to effect a myopia-reducing curvature correction of the eye.

45. The method of claim 43, in which said predetermined curvature profile is of circular symmetry and is characterized by ablation-depth penetration which is least at the center and greatest at the outer limit of said optically used central area, whereby to effect a hyperopia-reducing curvature correction of the eye.

46. The method of claim 43, in which said predetermined curvature profile is of circular symmetry and is characterized by ablation-depth penetration which is least at the center and greatest at the outer limit of said optically used central area, whereby to effect a hyperopia-reducing curvature correction of the eye, there being an annulus of exposed stroma tissue surrounding the outer limit of said optically used central area, and tissue-ablating laser radiation being applied within said annulus and with depth penetration in stroma tissue to a curvature profile which is continuous with said predetermined profile at the inner limit of said annulus and which reduces to substantially zero depth penetration at the outer limiti of said annulus.

47. The method of claim 43, in which said predetermined curvature profile is of lateral symmetry on opposite sides of a diametral alignment through said optically used central area, the orientation of said alignment being selected for correction of a diagnosed astigmatic condition of the eye.

48. The method of claim 43, in which said predetermined curvature profile is in an outer circular annulus concentric with the optical axis and within the optically used central area of said exposed body-stroma tissue, the predetermined curvature profile being of circular symmetry centered on the optical axis and characterized by ablation-depth penetration which is least at the inner radial limit of said annulus and greatest at the outer limit of said optically used area, whereby to improve the far-vision capability of a myopic eye.

49. The method of claim 43, in which said predetermined curvature profile is an outer circular annulus concentric with the optical axis and within the optically used central area of said exposed stroma tissue of the remaining body, the predetermined curvature profile being of circular symmetry centered on the optical axis and characterized by ablation-depth penetration which is least at the inner radial limit of said annulus and greatest at the outer limit of said optically used area, whereby to improve the far-vision capability of a myopic eye, there being a second annulus of exposed stroma tissue surrounding the outer limit of said optically used central area, and tissue-ablating laser radiation being applied within said second annulus and with depth penetration in stroma tissue to a curvature profile at the inner limit of said second annulus, said penetration reducing to substntially zero depth the outer limit of said second annulus.

50. The method of claim 43, in which said predetermined curvature profile is to a first curvature in an outer annular area concentric with the optical axis and within the optically used central area of said exposed body-stroma tissue and to a second curvature in the inner area that is contiguous to and surrounded by said annular area, both curvatures (1) being of circular symmetry centered on the optical axis and (2) being characterized by ablation-depth penetration which increases with increasing radial off set from said axis, the depth-penetration increase per unit radial-offset increase in said inner area exceeding the depth-penetration increase per unit radial-offset increase in said outer area.

51. The method of claim 43, in which the tissue-ablating laser radiation is in the ultra-violet wavelength region of the spectrum, for photo-chemical ablation of involved stroma tissue.

52. The method of claim 43, in which the tissue-ablating laser radiation is in the infrared wavelength region of the spectrum, for photo-thermal ablation of involved stroma tissue.

53. A method according to claim 43 further comprising the step of:

applying downward force loading of the lenticle in stroma-to-stroma contact with the resulting stroma surface, said force loading achieving pliant adaptation of the lenticle to the curvature profile of said resulting stroma surface.

* * * * *